US00PP08316P

United States Patent [19]

Drewlow

[11] Patent Number: Plant 8,316

[45] Date of Patent: Jul. 20, 1993

[54] IMPATIENS PLANT NAMED CAMEO

[75] Inventor: Lyndon W. Drewlow, Ashtabula, Ohio

[73] Assignee: Mikkelsens, Inc., Ashtabula, Ohio

[21] Appl. No.: 858,395

[22] Filed: Mar. 26, 1992

[51] Int. Cl.[5] ..... A01H 5/00
[52] U.S. Cl. ..... Plt./87.6
[58] Field of Search ..... Plt./87.6

*Primary Examiner*—James R. Feyrer
*Assistant Examiner*—Erich Veitenheimer
*Attorney, Agent, or Firm*—Foley & Lardner

[57] ABSTRACT

A distinct cultivar of impatiens plant named Cameo, characterized by its relatively large pink flowers, variegated leaves of bright and light green, with cream variegation around midrib in the basal region also appearing under high light conditions, excellent self-branching and basal branching, semi-upright growth habit, and its floriferous habit.

1 Drawing Sheet

The present invention relates to a new and distinctive cultivar of Impatiens plant, botanically known as Impatiens, commercially known as New Guinea Impatiens, and known by the cultivar name Cameo. Cameo was developed by me through controlled breeding by crossing Mikkelsen Seedling No. 88-204-10 (seed parent) with Mikkelsen Seedling No. 87-759-2 (pollen parent).

Asexual reproduction by terminal or stem cuttings has shown that the unique features of this new impatiens are stabilized and are reproduced true to type in successive propagations.

The following combination of characteristics distinguish the new impatiens from both its parent varieties and other cultivated impatiens of this type known and used in the floriculture industry. The cultivars Charade (U.S. Plant Pat. No. 7,787) and Meteor (not patented) are referred to for comparison purposes.

1. Cameo has pink flowers, (51A to 52A) with Charade having salmon flowers (39A) and Meteor salmon orange flowers (43C).
2. Cameo has slightly larger flowers at 6.5 to 7.0 cm diameter than Charade (6.0 to 6.5 cm) and much larger than Meteor (5.0 to 5.5 cm).
3. Midrib and major veins on underside of Cameo are light green while Meteor has a reddish pink midrib and major veins, especially on young leaves. Charade has reddish purple midrib and major veins on underside of leaf.
4. Flower spurs on all three cultivars are reddish in color, but Cameo and Charade have green tips and Meteor has a deep reddish tip.
5. Both Cameo and Meteor have bright green leaves with cream variegation around the midrib in the basal region of leaf under high light conditions. Meteor is more variegated. Charade has dark green leaves with a purple cast and no variegation.
6. Flower pedicels of Cameo and Charade are light green in color while the flower pedicel of Meteor has a pinkish red cast.
7. Cameo is intermediate in height (at 20 to 25 cm) between Charade (15 to 20 cm) and Meteor (25 to 30 cm).
8. Cameo has a semi-upright growth habit which is intermediate between the more mounded Charade and the more upright Meteor.

9. Cameo and Charade are similar in bloom date, with both being 7 to 10 days earlier than Meteor.
10. Cameo is much more self-branched and has better basal branching than Meteor.

The accompanying color photograph is a front perspective view illustrating the overall appearance of Cameo, with the colors being as nearly true as is reasonably possible to obtain in a colored reproduction of this type. The photograph was taken on Apr. 15, 1991 under natural light on an overcast day, under double poly greenhouse covering at Ashtabula, Ohio.

The following is a detailed description of my new cultivar, based on plants produced in greenhouses in Ashtabula, Ohio during the Fall and early Winter seasons of the year. Plants were grown in 10 cm pots and measurements were taken 12 weeks after rooted cuttings were planted. Height measurements were taken from the soil line of the container. The plants were grown at 65°–68° F. night temperatures, under 3000 to 4000 foot candles of light, and with nutritional values of 250 ppm nitrogen, 75 ppm potassium, and 250 ppm phosphorous, with trace elements added. Habit of growth, foliage coloration, leaf variegation, size of leaves and flower size will be influenced by nutritional and environmental conditions, without, however, any variation in the phenotype.

Color references are made to The Royal Horticultural Society Colour Chart except where general terms of ordinary dictionary significance are used.

Parentage: A controlled cross between female parent Mikkelsen Seedling No. 88-204-10 and male parent Mikkelsen Seedling No. 87-759-2.

Propagation:

A. *Type cutting.*—Stem tip 15 mm long will develop to 4 to 5 cm long in 18 to 21 days.

B. *Time to root.*—8–10 days at 23° C. summer; 10–12 days at 20° C. winter.

C. *Rooting habit.*—Heavy, fibrous.

Plant description:

A. *Form and habit of growth.*—Semi-tall; intermediate in height; highly self-branched; continuous flowering, vigorous growing, flowering herb with flowers above leaf canopy.

B. *Foliage description.*—Dark green with light green midrib. Under high light conditions cream variegation around midrib toward basal area of leaf. 1. Size: Mature average leaf is 12 to 13 cm long and 3.5 to 4.0 cm wide. 2. Shape: Lanceolate with acuminate apex and acute base. 3. Texture: Both upper and lower surfaces are glabrous. 4. Margin: Finely serrated with fine ciliate. 5. Color: young foliage, top side 137A. under side 146A. mature foliage, top side 147A. under side 147B. 6. Venation: Pinnate, green in color.

Flowering description:

A. *Flowering habits.*—Flowers continuously from leaf whorl in a progressively orderly manner, with one flower per leaf axil. When the last flower in a leaf whorl opens the first flower in the leaf whorl above starts to open. It takes 5 to 7 days for a mature bud to fully open and then the flower may last two weeks or longer depending on the environment.

B. *Natural flowering season.*—Indeterminant and continuous; quantity of flowers increases with increasing levels of light.

C. *Flower buds.*—Ellipsoidal, flowers perfect; reddish purple spur with green tip 4.5 cm long with the throat behind the ovary and originating from the major sepal.

D. *Flowers borne.*—On individual green pedicels from a whorl of usually five leaves, flowering progressively around the whorl as buds and leaves develop. Most leaf axils have one flower.

E. *Quantity of flowers.*—Very floriferous because of highly self-branching nature of plant and long lasting flowers which results in flowers being open at two leaf whorls at one time.

F. *Diameter of flower.*—6.5 to 7.0 cm.

G. *Petals.*—1. Shape: Heart, with keel being largest petal. 2. Color: Top side in winter when opening, 51A to 52A, fading to 51B; underside 52C. 3. Number of petals: 5. 4. Size of petals: Standard: 4.0 cm wide by 3.0 cm long; two equal lobes shallow cut. Wings: 3.0 cm wide by 3.0 cm long; two unequal lobes, intermediate cut. Keel: 3.5 cm wide by 3.75 cm long; two unequal lobes, deep cut.

H. *Reproductive organs.*—1. Stamens: Five (5) in number. a. Anther shape: Hooded, color cream with reddish tint. b. Pollen color: Cream. 2. Pistils: a. Stigma shape: Five segmented column, color whitish green. b. Style color: Whitish green. c. Ovaries: Five (5) in number, size 5 mm mature, color green.

*Disease resistance.*—No significant disease and insect problems to date.

Other Important Characteristics

1. Cameo has shown the ability to tolerate both high temperatures and sunlight levels and continue to flower, as well as cool temperatures (40°-50° F.). Thus its growing season can be expanded.

2. Early flowering, self-branching nature allows cultivar to be grown in a 10 cm pot, but Cameo is also vigorous enough so that it can be grown in 15 to 25 cm containers as well.

I claim:

1. A new and distinct impatiens plant named Cameo, as illustrated and described.

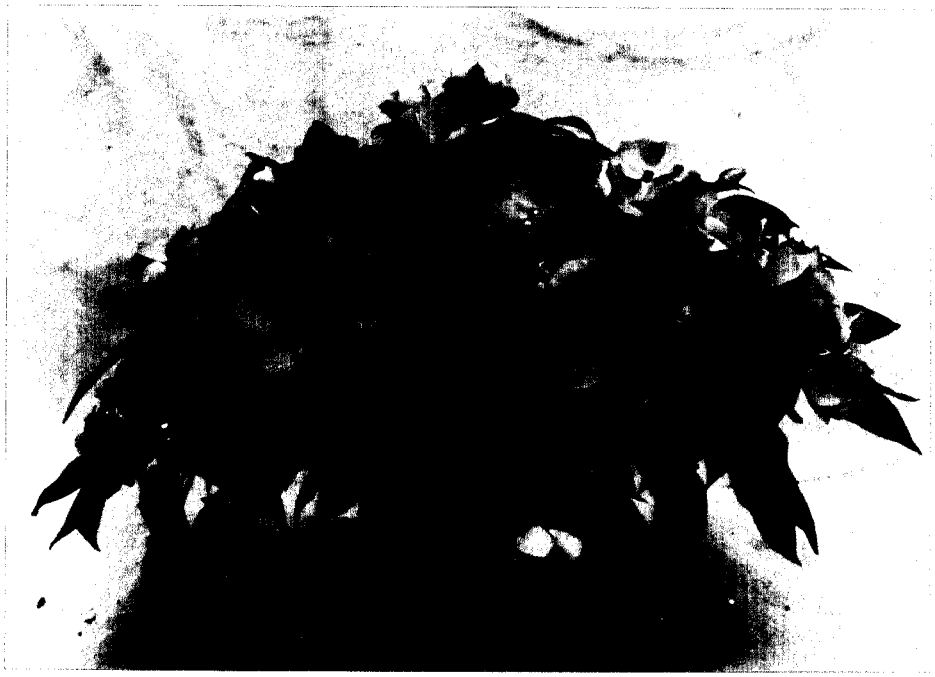

* * * * *